United States Patent [19]

Langer et al.

[11] Patent Number: 5,298,659

[45] Date of Patent: Mar. 29, 1994

[54] METHOD FOR THE PREPARATION OF AZOMETHINES

[75] Inventors: Reinhard Langer; Hans-Josef Buysch, both of Krefeld; Paul Wagner, Duesseldorf, all of Fed. Rep. of Germany

[73] Assignee: Bayer Aktiengesellschaft, Leverkusen, Fed. Rep. of Germany

[21] Appl. No.: 4,349

[22] Filed: Jan. 14, 1993

[30] Foreign Application Priority Data

Jan. 22, 1992 [DE] Fed. Rep. of Germany ....... 4201605

[51] Int. Cl.⁵ .......................................... C07C 249/02
[52] U.S. Cl. .................................... 564/271; 546/300; 546/304; 548/189; 548/198; 548/228; 548/229; 548/234; 548/320.1; 548/326.5; 548/333.1; 548/370.1; 548/371.7; 548/550; 548/559; 548/560; 549/65; 549/68; 549/480; 549/491; 564/276; 564/277

[58] Field of Search ................ 564/277, 271, 276; 546/300, 304; 548/189, 198, 228, 229, 234, 320.1, 326.5, 333.1, 370.1, 371.7, 550, 559, 560; 549/65, 68, 480, 491

[56] References Cited

U.S. PATENT DOCUMENTS

| | | | |
|---|---|---|---|
| 2,268,418 | 12/1941 | Paul | 564/277 |
| 2,336,215 | 12/1943 | Bean | 564/276 |
| 4,045,486 | 8/1977 | Krall et al. | 260/566 R |
| 4,281,195 | 7/1981 | George | 564/271 |

FOREIGN PATENT DOCUMENTS

| | | |
|---|---|---|
| 0014264 | 8/1980 | European Pat. Off. . |
| 0470460 | 2/1992 | European Pat. Off. . |
| 1078119 | 9/1960 | Fed. Rep. of Germany . |
| 1134076 | 8/1962 | Fed. Rep. of Germany . |
| 2166941 | 5/1977 | Fed. Rep. of Germany . |
| 2313354 | 12/1976 | France . |

OTHER PUBLICATIONS

Berichte Der Deutschen Chemischen Gesellschaft; pp. 344-355, 53, (1920).

*Primary Examiner*—Allen J. Robinson
*Assistant Examiner*—Peter G. O'Sullivan
*Attorney, Agent, or Firm*—Sprung Horn Kramer & Woods

[57] ABSTRACT

Azomethines can be prepared by the condensation of cycloalkanones and anilines in the presence of acid homogeneous catalysts while the water of reaction is removed azeotropically, the condensation being carried out in a continuous reaction in a column-like reactor to which a temperature profile is applied, the starting materials being fed in in the low-temperature region, and, of the reaction products, the water of reaction to be removed azeotropically being discharged also in the low-temperature region and the azomethine produced being discharged in the high-temperature region.

18 Claims, No Drawings

METHOD FOR THE PREPARATION OF AZOMETHINES

BACKGROUND OF THE INVENTION

1. Field of the Invention

The invention relates to a method for the preparation of N-cycloalkylideneanilines by elimination of water catalysed by acid and by azeotropic removal of the water of reaction.

The method comprises the reaction of optionally ring-substituted anilines with optionally substituted cycloalkanones in the presence of at least one acid catalyst which is soluble in mixtures of aniline/cycloalkanone/azomethine, at a raised temperature in a distillation column.

The condensation of aromatic amines with cycloalkanones is an equilibrium reaction with a small heat of reaction. It is shifted towards the azomethine (Schiff base) if the water generated in the reaction is removed from the system. In general this is achieved by azeotropic distillation, an inert entrainer such as benzene, toluene etc. being used if required.

2. Description of the Related Art

More recently, the binding of the water of reaction by using $TiCl_4$ (J. Org. Chem. 32 (1967), 3247) or molar quantities of $(butyl)_2SnCl_2$ (Synth. Commun. 12 (1982), 495) has been described. Both these compounds bind the water of reaction produced while liberating HCl.

In other developments, the species binding the water is bound covalently to the aniline, for example in the form of N,N-bis-(trimethylsilyl)-aniline (Bull. Soc. Chim. Fr. 1966, 3205), iminophosphoranes (Angew. Chem. Int. Ed. Eng. 5 (1966), 947) and N-(diphenylaluminium)-aniline (J. Org. Chem. 51 (1986), 1848).

A further method of binding effectively the water of reaction produced and thus being able to work under mild conditions, using small excess amounts of aniline or ketone, is to use molecular sieves (J. Org. Chem. 36 (1971), 1570; German Offenlegungsschrift 2 244 238). The disadvantage of this last-mentioned method is the laborious and expensive regeneration of the molecular sieve.

Azeotropic dehydration is certainly the method of greatest industrial interest if it is possible to carry out the reaction with low energy expenditure, a good space-time yield and selectivity, and without excessive quantities of azeotropic entrainer in a simple apparatus.

High space-time yields require as a precondition a high reaction rate, and therefore effective catalysis.

The condensation of cyclohexanone and aniline to give cyclohexylideneaniline, using zinc chloride as a catalyst, has long been known (Ber. 53 (1920) 345-354). In difficult cases of condensations of this type, the catalyst system $HCl-ZnCl_2$ has been used (Ber. 46 (1913) 2718). German Auslegeschrift 1 078 119 describes the condensation N-phenyl-p-phenylene-diamine with cyclohexanone without the addition of a catalyst; in such cases the use of a cyclohexanone excess of 200 to 300% is required.

German Offenlegungsschrift 2 525 295 discloses that the reaction time of the condensation of aniline, using a 400% excess of cyclohexanone without a catalyst, increases sharply with increasing batch size, making it impossible to scale up to industrial level. It was also disclosed that strongly and weakly acid organic resins affect the reaction time favourably.

German Offenlegungsschrift 2 901 863 describes freshly synthesised, anhydrous, non-calcined calcium hydrogen-phosphate, apatite of the formula $Ca_5(PO_4)_3OH$, dried, non-roasted aluminium oxide hydroxides and proton-exchanged aluminium silicates washed to neutrality of the montmorillonite type as effective catalysts for the reaction of aromatic amines with ketones. The examples in this patent application are limited, however, to the condensation of the reactive p-phenylenediamine with methyl isobutyl ketone, a 150% excess of ketone being used.

All the abovementioned methods for azomethine synthesis by azeotropic dehydration have the drawback that it is both time-consuming and energetically expensive to take the reaction to completion.

It was therefore desirable to develop a cost-effective and environmentally friendly method for the synthesis of cycloalkylideneanilines, which method is to be notable for high yields, simple apparatus and optimum energy utilisation with minimum energy consumption.

SUMMARY OF THE INVENTION

A method has been found in which the starting materials, with a minimum excess of carbonyl component or aniline component, are fed into a reactor which operates continuously and from which the azomethine compound can be taken directly in high yield and with high purity.

A method for the preparation of azomethines of the formula

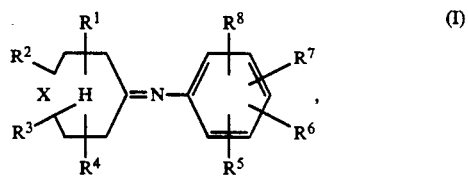

in which $R^1$, $R^2$, $R^3$, $R^4$, $R^5$, $R^6$, $R^7$ and $R^8$, independently of one another, represent hydrogen, straight-chain or branched $C_1$–$C_6$-alkyl, $C_3$–$C_6$-cycloalkyl or aryl and $R^5$, $R^6$, $R^7$ and $R^8$, independently of one another, additionally represent halogen, straight-chain or branched $C_1$–$C_6$-alkoxy, hydroxyl, amino, $C_1$–$C_6$-alkylamino, di-$C_1$–$C_6$-alkyl-amino, aryloxy or arylamino, in which aryl represents phenyl or 5- or 6-membered heteroaryl having 1 or 2 heteroatoms from the group N, O and S which is linked in the 2-, 3- or 4-position, and X represents —$CH_2$— or a bond connecting the neighbouring C atoms, by condensation of cycloalkanones of the formula

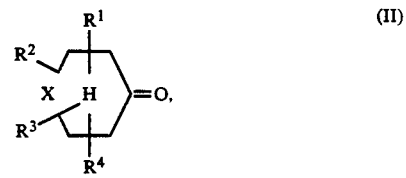

with anilines of the formula

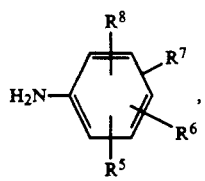

(III)

in which $R^1$ to $R^8$ and X have the abovementioned meaning, has been found, which is characterised in that the condensation is carried out in a continuous reaction in a distillation column in the presence of acid homogeneous catalysts having a $pK_a$ value measured in $H_2O$ of 1 to 6, while the water of reaction is removed azeotropically, the starting materials, the azeotropic agent and the catalyst or the catalyst mixture being fed separately at different locations, or together as a mixture at the same location, into the distillation column, and, of the reaction products, the water to be removed azeotropically being discharged from the low-temperature region and the azomethine produced being discharged from the high-temperature region.

DETAILED DESCRIPTION OF THE INVENTION

In a preferred embodiment, starting materials are used in which aryl represents phenyl.

In another preferred embodiment, cycloalkanones are used in which $R^4$ represents hydrogen.

In yet another preferred embodiment, anilines are used in which $R^8$ represents hydrogen.

In a particularly preferred embodiment, cycloalkanones are used in which $R^3$ and $R^4$ represent hydrogen.

In a similarly particularly preferred embodiment, anilines are used in which $R^7$ and $R^8$ represent hydrogen.

Furthermore, cycloalkanones of the formula

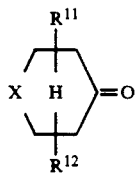

(IV)

are preferred in which $R^{11}$ and $R^{12}$, independently of one another, represent hydrogen, straight-chain or branched $C_1$-$C_4$-alkyl, cyclopropyl, cyclopentyl, cyclohexyl or phenyl and X represents —$CH_2$— or a bond connecting the neighbouring C atoms.

In a particularly preferred embodiment, cycloalkanones of the formula

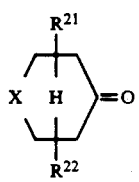

(V)

are used in which $R^{21}$ and $R^{22}$, independently of one another, represent hydrogen, methyl or ethyl and X has the abovementioned meaning.

In a preferred embodiment, furthermore, anilines of the formula

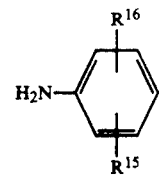

(VI)

are used in which $R^{15}$ and $R^{16}$, independently of one another, represent hydrogen, straight-chain or branched $C_1$-$C_4$-alkyl, phenyl, fluorine, chlorine, bromine, straight-chain or branched $C_1$-$C_4$-alkoxy, hydroxyl, amino, $C_1$-$C_4$-alkylamino, di-$C_1$-$C_4$-alkyl-amino, phenoxy or phenylamino.

In a particularly preferred embodiment, anilines of the formula

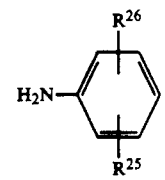

(VII)

are used in which $R^{25}$ and $R^{26}$, independently of one another, represent hydrogen, methyl, ethyl, fluorine, chlorine, methoxy, ethoxy, methylamino, ethylamino, dimethylamino or diethylamino.

In a most particularly preferred embodiment, anilines of the formula

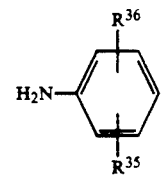

(VIII)

are used in which $R^{35}$ and $R^{36}$, independently of one another, represent hydrogen, fluorine, chlorine, methyl, ethyl, methoxy, methylamino or dimethylamino.

Alkyl groups to be mentioned in the said substituents (alkyl, alkoxy, alkylamino, dialkylamino) are straight-chain or branched $C_1$-$C_6$-alkyl groups, such as methyl, ethyl, propyl, isopropyl, butyl, isobutyl, tert-butyl and the isomeric pentyls and hexyls. Preferably to be mentioned are the said $C_1$-$C_4$-alkyl groups, particularly preferably methyl and ethyl, most particularly preferably methyl.

Aryl to be mentioned in the said substituents (aryl, aryloxy, arylamino) is phenyl or a 5- or 6-membered heteroaryl having 1 or 2 heteroatoms from the group N, O and S which is linked in the 2-, 3- or 4-position. Examples of such a heteroaryl are: furanyl, pyrrolyl, thienyl, pyrazolyl, imidazolyl, oxazolyl, thiazolyl, pyridyl and others. In a preferred embodiment, aryl represents phenyl.

$C_3$-$C_6$-cycloalkyl to be mentioned is, for example, cyclopropyl, cyclobutyl, cyclopentyl and cyclohexyl, preferably cyclopropyl, cyclopentyl and cyclohexyl.

The cycloalkyl substituents, in their turn, may be singly or doubly substituted by methyl or ethyl.

Halogen to be mentioned is, for example, fluorine, chlorine, bromine, iodine, preferably fluorine, chlorine, bromine, particularly preferably fluorine and chlorine.

The expression "X" in the cycloalkyl ring in the formulae (I), (II), (Iv) and (V) may represent the methylene group —$CH_2$— or a bond connecting the neighbouring C atoms. In the first case, this denotes the cyclohexane skeleton, in the second case the cyclopentane skeleton. In a preferred embodiment, X represents the methylene group and thus constitutes the cyclohexane skeleton.

The following specific cycloalkanones may be mentioned as starting compounds by way of example: cyclopentanone, 2-methyl-cyclopentanone, 2-ethyl-cyclopentanone, 2-phenyl-cyclopentanone, cyclohexanone, 2-methyl-cyclohexanone, 4-methyl-cyclohexanone, 2-ethylcyclohexanone, 4-ethyl-cyclohexanone, 4-phenyl-cyclohexanone, 2-phenyl-cyclohexanone, 4-cyclohexyl-cyclohexanone, 2-cyclohexyl-cyclohexanone.

The following specific anilines may be mentioned as starting compounds by way of example: aniline, 2-methylaniline, 3-methylaniline, 4-methylaniline, 2,4-dimethyl-aniline, 2-ethylaniline, 4-ethylaniline, 3-methoxyaniline, 3-ethoxyaniline, 4-aminoaniline, 4-methylamino-aniline, 4-dimethylamino-aniline, 4-phenylaniline, 2-phenylaniline, 4-phenoxyaniline, 2-phenoxyaniline, 4-phenylamino-aniline, 2-phenylaminoaniline, 2-fluoroaniline, 4-fluoroaniline, 2-chloroaniline, 4-chloroaniline.

The molar ratio in which the cycloalkanone and the aniline are metered in is 2:1 to 1:2, preferably 1.5:1 to 1:1.5, particularly preferably 1.2:1 to 1:1.2, most particularly preferably 1.1:1 to 1:1.1.

In order to remove the water of reaction azeotropically, azeotropic agents may be used from the group of the aliphatic and aromatic hydrocarbons, the aliphatic and aromatic ethers and the aliphatic alcohols. In these compounds, hydrogen atoms may be replaced by halogen atoms. These azeotropic agents, their mode of action and their use are, in principle, known to those skilled in the art. Azeotropic agents to be mentioned by way of example are the following:

benzene, toluene, xylene, anisole, chlorobenzene, butanol, hexanol, methyl butyl ether, diphenyl ether, p-chloroanisole. The weight ratio in which an azeotropic agent and the sum of the starting materials are metered in is 0.001–1:1, preferably 0.001–0.5:1, particularly preferably 0.001–0.2:1, most particularly preferably 0.001–0.1:1. In a way known to those skilled in the art, the azeotrope which has been distilled off can be condensed outside the column-type reactor and can separated into the water of reaction and the azeotropic agent. The azeotropic agent thus recovered can again be recycled into the reaction of the method according to the invention.

It is also possible to use, as the azeotropic agent, one of the starting materials, preferably the cycloalkanone, which makes it possible to dispense with an azeotropic agent foreign to the system.

Possible acid homogeneous catalysts are, in principle, all inorganic or organic compounds are used which have a $pK_a$ value, measured in $H_2O$, from 1–6, preferably from 2–5.5, particularly preferably from 3–5. Preferably, alkylcarboxylic acids or arylcarboxylic acids are used in their pure form or as mixtures.

Particularly preferably, $C_{1-10}$-, most particularly preferably $C_{2-6}$-carboxylic acids, are used in their pure form or as mixtures.

Examples to be mentioned are: formic acid, acetic acid, propionic acid, butyric acid, benzoic acid, valeric acid and isobutyric acid.

If the sum of the acid groups of the metered catalytically active acids is considered in proportion to the sum of the metered starting material molecules, the metered amount of acid varies within the range from 10 to 0.001 mol %, preferably from 1 to 0.01 mol %, particularly preferably from 0.5 to 0.02 mol %.

Acid mixtures are used in this context which are removed, to at least 50%, preferably to at least 70%, particularly preferably to at least 90%, together with the azeotropic gas phase, from the low-temperature region of the reactor.

This is expedient because of the fact that large amounts of acid in the high-temperature region may give rise to the condensation of azomethine molecules with the elimination of aniline, and because they should therefore be kept away to a large extent from this region of the reactor. This is achieved by making use of the distillation process taking place in the reactor in the method according to the invention; accordingly, for each of the substrate combinations claimed, an optimum solution in each individual case is to be found by experimental means from the acid combinations claimed.

The method according to the invention is characterised by the condensation being carried out in a distillation apparatus suitable for continuous operation.

Such an apparatus, in the simplest case, comprises an isolated column with a condenser and flow divider at the column head (end of the low-temperature region) and an evaporator of any design arranged for continuous product discharge at the bottom of the column (end of the high-temperature region of the distillation apparatus).

The column may, according to the processes taking place therein, by definition be divided into three sections: in the upper section (the low-temperature region), the separation of starting materials and water of reaction is the main process taking place; in the lower section (the high-temperature region), the product is separated from unreacted starting material and catalyst residues: in the middle section, the reaction range, the starting materials and, where possible, the catalysts from the other two regions are combined and reacted with the elimination of water.

As the reaction is, at best, weakly exothermic, and the water produced has to be transferred into the gas phase with a relatively high energy expenditure and, at the same time, starting material molecules, according to their partial vapour pressures, must also be evaporated, the reaction section requires an energy infeed which, in general, is greater than the energy required for the separation of unreacted starting material from the azomethine.

In a special embodiment of the method, below the reaction zone a heat exchanger is therefore installed which evaporates most of the unreacted starting material in order to supply the insulated reaction part with energy and to relieve the high-temperature region of this requirement. If necessary, the reaction part may, at a suitable location, additionally be supplied with more energy, generally at that location where most of the reaction takes place and where, therefore, the largest amount of water is formed. These additional energy input locations not only relieve the high-temperature region of the column: they also allow the input of a considerable fraction of the energy required at a low thermal level.

Above the reaction part, a heat exchanger may be installed, if required, which separates unreacted starting material by condensation, with energy recovery if possible, from the water of reaction and which thus relieves the low-temperature region in which the azeotrope is formed.

The design of the individual regions is a standard process engineering problem which is solved by known methods for each individual case by experiments and calculations.

The three sections of the column, according to the design of the apparatus, may have different cross-sectional areas, in order to take account of the different gas and liquid loads prevailing therein.

Without an evaporator part below the reaction zone, all of the energy required for reaction and separation must be fed into the system at the bottom of the column by the evaporation of azomethine and must be transported upwards from there as evaporation enthalpy, being used, successively, for the separation of starting material and product, and of water and starting material. This means that the lower volume part, in accordance with its high liquid and gas loading, has at least the same cross-sectional area, preferably 1.5 times the cross-sectional area, and at most three times, as a preferred maximum twice, the cross-sectional area of the reaction part.

If the reaction part is fitted at the bottom with an evaporator and at the top with a dephlegmator, both the low- and the high-temperature region are relieved and accordingly have at most the same cross-sectional area, preferably only two thirds, but at least one third, preferably at least half of the cross-sectional area of the reaction part.

The sizes depend not least on the column fillings selected for the various column zones (packings or fixed fillings which may be identical or different).

The packings to be used, which may be arranged packings, are those which are per se common for distillations, as they are described, for example, in Ullmanns Encyclopädie der Techn. Chemie [Ullmann's Encyclopedia of Industrial Chemistry] Vol. 2, p. 528 et seq. (4th Edition), or in company publications, for example from Sulzer, Montz, Raschig, Kühni or Norton.

To be mentioned, for example, are:

Raschig ® or Pall ® rings, Berl or Intalox ® toroidal saddles, Interpack ® packings made of various materials, such as glass, ceramic, porcelain, carbon, alloy steel, plastics, which, particularly in the case of metal, may be in a woven or mesh-like form.

Preferred are arranged packings and poured packings which have a large surface area and good wetting properties, in addition to sufficient residence time of the liquid, for example Pall ® and Novolax ® rings, Berl ® saddles, BX ® packings, Montz-Pak ®, Mellapak ®, Melladur ®, Kerapak ®, CY ® packings, Ralu-Pak ® and Rombo-Pak ®.

Suitable for the method according to the invention, however, are not only packed columns, but also, in particular, columns with fixed fillings.

Suitable are plate columns having sieve plates, bubble-cap plates, valve plates, tunnel-cap plates and centrifuge plates, which again may have various designs.

Preferred are, for example, bubble-cap and valve plates having high residence times accompanied by effective mass exchange; this applies, in particular, to the reaction part of the column.

The method according to the invention is carried out in a pressure range from 0.5 mbar to 3 bar, preferably from 1 mbar to 1 bar, particularly preferably at 2-250 mbar, most particularly preferably at 3-180 mbar. For the purpose of working in the preferred low-pressure range, the column-type reactor is equipped, at its upper low-temperature end, with a vacuum pump which may be connected upstream or downstream of the condenser for the water to be removed azeotropically.

In the distillation column a steady-state temperature profile is established. This temperature profile comprises the temperature range from 10° to 300° C., preferably 15° to 250° C., particularly preferably 20° to 200° C.

The temperature range of the reaction zone, the zone in which more than 90% of the water of reaction is liberated and which, if required, is fitted at its upper end with a dephlegmator and its lower end with an evaporator, is preferably 25° to 180° C., particularly preferably 35° to 160° C., most particularly preferably 45° to 140° C.

The pressure applied to a distillation column, together with the pressure build-up due to the flow resistance in the apparatus, determines the boiling points of the liquid mixtures inside the column.

If the reaction is slow, and if, in order to improve the space-time yield, the pressure in the reaction part and therefore the temperature in the reaction part is raised, the thermal load for the high-boiling reaction product at the end of the column increases at the same time.

If this creates problems, that is to say decomposition reactions occur, the high-temperature range may be subdivided if required by selecting the temperature at the lower end of the column in such a way that decomposition still does not take place, but that unreacted aniline and cycloalkanone are discharged at the same time. This mixture is freed, in a column (the second part of the high-temperature range) working in parallel at distinctly lower pressure, from residual aniline and cycloalkanone which, as the top product of this second distillation apparatus, are fed to the reaction column either after condensation or directly after compression.

The infeed position can be chosen at will anywhere in the reaction region (e.g. in the first part of the high-temperature region) or in the low-temperature region, preferably at that location where the ratio of aniline to cycloalkanone of the liquid phase in the reaction column is equal to that of the top product.

The pressure in this second part of the high-temperature region is preferably 1/1000 to 1/10, particularly preferably 1/100 to 1/10, of the working pressure of the reaction column.

The input materials may be fed into the reactor, individually or as a mixture, above the reaction zone at a location chosen at will in the low-temperature region. They are preferably fed in as a mixture immediately above the reaction zone. In a particularly preferred embodiment, the mixture is fed into the reactor at that point where the ratio of the materials used in the liquid phase in the reactor is equal to the ratio in the mixture to be fed in. In the case that one of the materials used, because of its greater volatility, is under-represented in the reaction zone, it can, however, also be fed in, wholly or in part, below the reaction zone or in the lower part of the reaction zone and thus, wholly or in part, be conveyed towards the other reactant in counter-current flow.

If a separate azeotropic agent is used, it can also be fed in separately from the starting materials; in a preferred embodiment, however, it is fed in together with the mixture of the starting materials or at least mixed with one of the starting materials.

The same applies to the catalyst or the catalyst mixture which is preferably metered in in a mixture with the starting materials, but which may also, if required, be conveyed towards the starting materials from the lower part of the apparatus, in which case care must be taken that little or no catalyst reaches the lowermost region of the column.

The azomethine as the reaction product is discharged at the lower reactor end in the high-temperature region, for example from the bottom circulation. The product is normally very pure and can be used subsequently without further purification. In the case that by-products of low volatility are to be separated, the desired azomethine may, in a way known in principle to the process engineer, be removed from the column-type reactor at a location above the discharge of such low-volatility by-products, which location is chosen such that maximum purity is ensured.

In a preferred embodiment, in counterflow to the azomethine withdrawn in the high-temperature region, an inert gas stream is fed in, also in the high-temperature region, i.e. in any case below the reaction zone. Inert gases to be mentioned are, for example: air, nitrogen, argon or methane, which are all preferably used in dried form.

At the upper end of the column-type reactor, that is in the low-temperature region, water of reaction is removed as an azeotrope and in a separating vessel is separated into an aqueous and an organic phase of the azeotropic agent. The organic phase, in a preferred embodiment, is recycled to the reactor, in particular if one of the reactants is also the azeotropic agent; this can be done at one of the abovementioned locations.

By means of this circular flow, a not inconsiderable amount of acid catalyst is returned to the reaction zone. This amount must be taken into account when metering the acid.

The acid content of an apparatus having circular flow is assessed most easily by measuring the pH of the aqueous phase of the distillate and keeping said pH constant by means of the catalyst infeed.

The advantage of the method according to the invention compared to the prior art consists in the possibility of using nearly equimolar amounts of the starting materials which can then be reacted completely in a single pass. This achieves a quantitative yield while avoiding additional working-up stages. The method to be used is notable for great simplicity and for optimum utilisation of the energy employed.

The azeomethines which can be prepared according to the invention are starting materials for the hydrogenation to give cyclohexyl-cycloalkyl-amines and phenyl-cycloalkyl-amines and, in the case that the cycloalkanone is a cyclohexanone, for the dehydrogenation to give optionally substituted diphenylamines.

EXAMPLE 1

The apparatus, from bottom to top, comprises: glass flask (250 ml) with regulated nitrogen inlet for receiving the bottom product (from this flask, the azomethine is obtained by being removed, from time to time, with suction); oil-thermostated coil evaporator (coil tube length approx. 1.50 m, internal diameter of tube approx. 1.5 cm); vacuum-mirrored packed column, filled with porcelain saddle packings 0.5 cm in size (internal diameter of column approx. 2.7 cm, height of the column approx. 35 cm); oil-thermostated column part, filled with porcelain saddle packings (diameter approx. 2.7 cm, height approx. 35 cm); oil-thermostated sieve plate column (internal diameter approx. 5 cm, height approx. 60 cm, 10 plates having in total a liquid volume of approx. 60 ml: the oil jacket was thermostated to a temperature which equalled the internal temperature of the column as closely as possible at all locations); infeed pipe (internal diameter approx. 2.7 cm, height approx. 5 cm); oil-thermostated column part with porcelain saddle packings (diameter (internal) approx. 2.7 cm, height approx. 15 cm); vacuum-mirrored packed column with porcelain saddle packings (internal diameter approx. 2.7 cm, height approx. 25 cm); air bridge to the down-flow condensing part, comprising two intensive condensers, Anschütz head, vacuum off-take connection and gas cap with vacuum tubing.

The vacuum in the apparatus was maintained by a diaphragm pump; evacuation was controlled by a vacuum controller having a regulatable ball valve ($\pm 0.5$ mbar).

Starting materials are metered in as mixtures by a vacuum-tight metering pump (TELAP, PTFE minidoser). The four thermostated column regions were heated, cooled or insulated by means of oil thermostats.

The pressure was set to 60 mbar, and an $N_2$ flow of 0.1 l/h S.T.P. was introduced into the lower part of the apparatus. After the oil thermostats had reached their required temperature (oil temperature of the lower evaporator approx. 195° C., oil temperature of the middle evaporator approx. 190° C., oil temperature of the sieve plate column approx. 80° C., oil temperature of the upper condenser approx. 20° C.), metering of the starting materials was initiated (330 ml/h). The starting materials consisted of 1.2 mol of cyclohexanone, 1 mol of aniline and 1 mol % (based on the two components) of acetic acid (117.6 g, 93 g, 1.32 g).

After a run time of about 1 to 2 hours, the apparatus was in equilibrium, and at the foot of the column, approx. 264 g of cyclohexylideneaniline having a purity of more than 99.9% were discharged from the coil evaporator per hour. The acetic acid content of the azomethine (anil) was below 10 ppm (determined by ion chromatography).

At the head of the columns, approx. 59 g of a cyclohexanone/water mixture condensed which separated, at a volume ratio of 1.1 to 1, into an organic and an aqueous phase. This mixture contained the catalyst.

EXAMPLE 2

The procedure of Example 1 was followed, but 0.2 mol % (264 mg) of acetic acid and 0.0004 mol % (0.65 mg) of propionic acid were added to the starting material mixture of 1.2 mol of cyclohexanone and 1 mol of aniline. The experiment proceeded as described in Example 1, but the equilibrium was only achieved completely after a somewhat longer run time. The cyclohexylideneaniline (purity better than 99.9%) similarly contained less than 10 ppm of acetic acid and less than 0.5 ppm (lower detection limit) of propionic acid.

EXAMPLE 3

If the catalyst content of Example 2 was further reduced, the establishment of the chemical equilibrium for the loading described proceeded too slowly, and as a result the major part of the starting material mixture fed in distilled off at the top.

EXAMPLE 4

As Example 2 but without propionic acid. Outcome similar to Example 3.

EXAMPLE 5

As Example 1, but 1 mol % of anhydrous HCl (803 mg) was admixed to the starting material mixture of 1.2 mol of cyclohexanone and 1 mol of aniline.

The course in this Example largely corresponded to that of Example 1, albeit with the difference that the temperature in the lower column part was 20° to 30° C. below that of Example 1 and, as the product, a mixture of 5% of unidentified high-boiling products, 48% of cyclohexenyl-cyclohexylideneaniline, 25% of cyclohexylideneaniline, 19% of aniline and 3% cyclohexanone was obtained.

What is claimed is:

1. A method for the preparation of an azomethine of the formula

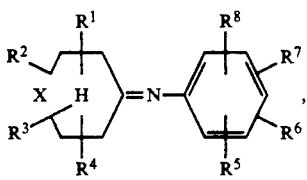

in which $R^1$, $R^2$, $R^3$, $R^4$, $R^5$, $R^6$, $R^7$ and $R^8$, independently of one another, represent hydrogen, straight-chain or branched $C_1$-$C_6$-alkyl, $C_3$-$C_6$-cycloalkyl, benzyl or aryl, and $R^5$, $R^6$, $R^7$ and $R^8$, independently of one another, additionally represent halogen, straight-chain or branched $C_1$-$C_6$-alkoxy, hydroxyl, amino, $C_1$-$C_6$-alkylamino, di-$C_1$-$C_6$-alkyl-amino, aryloxy or arylamino, in which aryl represents phenyl or 5- or 6-membered heteroaryl having 1 or 2 heteroatoms from the group N, O and S which is linked in the 2-, 3- or 4-position, and X represents —$CH_2$— or a bond connecting the neighboring C atoms, by condensation of a cycloalkanone of the formula

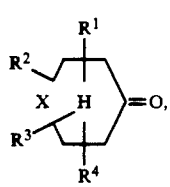

with an aniline of the formula

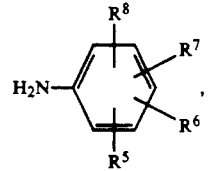

in which $R^1$ to $R^8$ and X have the abovementioned meaning, comprising carrying out said condensation in a continuous reaction in a distillation column in the presence of an acid homogeneous catalyst having a $pK_a$ value measured in $H_2O$ of 1 to 6, while the water of reaction is removed azeotropically, the starting materials, the azeotropic agent and the catalyst or a catalyst mixture being fed separately at different locations, or together as a mixture at the same location, the cycloalkanone and analine being fed at a molar ratio of from 2:1 to 1:2 with respect to each other and the catalyst or catalyst mixture being fed at a molar ratio of from 10 to 0.001 mol % with respect to the total amount of feed, into the distillation column, and, of the reaction products, the water of reaction to be removed azeotropically being discharged from the low-temperature region and the azomethine produced being discharged from the high-temperature region, and wherein the temperature profile in the column-type reaction is in the range of from 10° to 300° C. and the pressure of from 0.5 mbar to 3 bar;

2. The method of claim 1, wherein a cycloalkanone of the formula

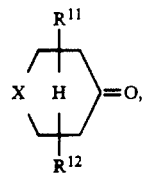

is used in which $R^{11}$ and $R^{12}$, independently of one another, represent hydrogen, straight chain or branched $C_1$-$C_4$-alkyl, cyclopropyl, cyclopentyl, cyclohexyl, benzyl or phenyl and X represents —$CH_2$— or a bond connecting the neighbouring C atoms.

3. The method of claim 2, wherein a cycloalkanone of the formula

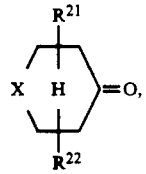

is used in which $R^{21}$ and $R^{22}$, independently of one another, represent hydrogen, methyl or ethyl and X has the abovementioned meaning.

4. The method of claim 1, wherein the cycloalkanone is a cyclohexanone.

5. The method of claim 1, wherein an aniline of the formula

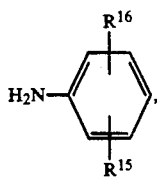

is used in which

R[15] and R[16], independently of one another, represent hydrogen, straight-chain or branched $C_1$-$C_4$-alkyl, phenyl, fluorine, chlorine, bromine, straight-chain or branched $C_1$-$C_4$-alkoxy, hydroxyl, amino, $C_1$-$C_4$-alkylamino, di-$C_1$-$C_4$-alkyl-amino, phenoxy or phenylamino.

6. The method of claim 5, wherein an aniline of the formula

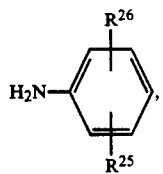

is used in which

R[25] and R[26], independently of one another, represent hydrogen, methyl, ethyl, fluorine, chlorine, methoxy, ethoxy, methylamino, ethylamino, dimethylamino or diethylamino.

7. The method of claim 6, wherein an aniline of the formula

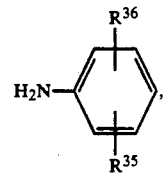

is used in which

R[35] and R[36], independently of one another, represent hydrogen, fluorine, chlorine, methyl, ethyl, methoxy, methylamino or dimethylamino.

8. The method of claim 1, wherein the cycloalkanone and the aniline are used in a molar ratio of 1.5:1–1:1.5.

9. The method of claim 8, wherein the cycloalkanone and the aniline are used in a molar ratio of 1.2:1–1:1.2.

10. The method of claim 1, wherein the catalyst or catalyst mixture is in the range of 1 to 0.01 mol %.

11. The method of claim 1, wherein the temperature profile in the column-type reactor is int he range from 15° to 250° C.

12. The method of claim 11, wherein the temperature profile is in the range of from 20° to 200° C.

13. The method of claim 1, wherein in counterflow to the azomethine withdrawn in the high-temperature region, an inert gas flow is fed in, also in the high-temperature region.

14. The method of claim 1, wherein a pressure form 1 mbar to 1 bar is used.

15. The method of claim 14, wherein a pressure from 3 to 180 mbar is used.

16. The method of claim 1, wherein as acid homogeneous catalyst, inorganic or organic compounds are used which have a $pK_a$ value, measured in water, from 1 to 6.

17. The method of claim 16, wherein, as acid homogeneous catalysts alkylcarboxylic or arylcarboxylic acids having 1 to 10 C atoms are used.

18. The method of claim 17, wherein the alkylcarboxylic acids have 2 to 6 C atoms.

* * * * *

UNITED STATES PATENT AND TRADEMARK OFFICE
CERTIFICATE OF CORRECTION

PATENT NO. : 5,298,659
DATED : March 29, 1994
INVENTOR(S) : Reinhard LANGER, et al.

It is certified that error appears in the above-identified patent and that said Letters Patent is hereby corrected as shown below:

Column 14, line 21,     cancel "int he" and substitute --in the--

Column 14, line 29,     cancel "form" and substitute --from--

Signed and Sealed this

Sixth Day of April, 1999

Attest:

Q. TODD DICKINSON

Attesting Officer     Acting Commissioner of Patents and Trademarks